(12) United States Patent
Kawabe et al.

(10) Patent No.: US 6,187,972 B1
(45) Date of Patent: Feb. 13, 2001

(54) PROCESS FOR PRODUCING AN ALKYLENE GLYCOL

(75) Inventors: Kazuki Kawabe, Yokkaichi; Kouichi Nagata, Kitakyusyu, both of (JP)

(73) Assignee: Mitsubishi Chemical Corporation, Tokyo (JP)

( * ) Notice: Under 35 U.S.C. 154(b), the term of this patent shall be extended for 0 days.

(21) Appl. No.: 09/369,893

(22) Filed: Aug. 9, 1999

(30) Foreign Application Priority Data

| Aug. 10, 1998 | (JP) | 10-225601 |
| Sep. 3, 1998 | (JP) | 10-248933 |
| Nov. 13, 1998 | (JP) | 10-323147 |

(51) Int. Cl.[7] .................. C07C 29/09; C07C 29/80
(52) U.S. Cl. .................. 568/858; 568/852; 568/868; 549/230
(58) Field of Search ............... 549/230; 568/852, 568/858, 868

(56) References Cited

U.S. PATENT DOCUMENTS 4,283,580 * 8/1981 Odanaka et al. .................. 568/858

* cited by examiner

*Primary Examiner*—Peter O'Sullivan
(74) *Attorney, Agent, or Firm*—Oblon, Spivak, McClelland, Maier & Neustadt, P.C.

(57) ABSTRACT

A process for producing an alkylene glycol, which is a continuous process for producing an alkylene glycol comprising the following steps (1) to (4), wherein the hydrolysis step (2) is divided into a plurality of stages, and the hydrolysis is carried out so that the water concentration in a reaction stage wherein the conversion of the alkylene carbonate is at least 60%, is from 15 to 30 wt %:

(1) a carbonating step of reacting an alkylene oxide with carbon dioxide gas in the presence of a carbonating catalyst to form a reaction solution containing an alkylene carbonate, (2) a hydrolysis step of hydrolyzing the reaction solution obtained in step (1) while releasing carbon dioxide gas, to form an aqueous alkylene glycol solution, (3) a distillation step of distilling the aqueous alkylene glycol solution to obtain at least a dehydrated alkylene glycol and a solution containing the carbonating catalyst, and (4) a recycling step of supplying the solution containing the carbonating catalyst to the carbonating step (1).

10 Claims, 1 Drawing Sheet

PROCESS FOR PRODUCING AN ALKYLENE GLYCOL

BACKGROUND OF THE INVENTION

1. Field of the Invention

The present invention relates to a process for producing an alkylene glycol from an alkylene oxide. More particularly, it relates to a process for producing an alkylene glycol with especially high efficiency.

2. Discussion of Background

An alkylene glycol, particularly ethylene glycol, is used, for example, as a raw material for synthetic fibers or resins, or as an anti-freezing liquid, and is an industrially important compound.

As a way for producing an alkylene glycol, a process of hydrolyzing an alkylene carbonate, is well known. Such a reaction is usually carried out in the presence of a catalyst for hydrolysis, and it has been proposed to use a catalyst for hydrolysis such as an alkali metal carbonate (U.S. Pat. No. 4,117,250), a molybdenum compound (JP-B-55-154927) or a tungsten compound (JP-B-55-154928) in order to increase the reaction rate.

By the use of these catalysts for hydrolysis, the hydrolysis can be accelerated, but the degree of acceleration has not been adequate. If the reaction is carried out at a higher temperature to accomplish an industrially satisfactory reaction rate, there has been a problem that the quality of the product tends to deteriorate. On the other hand, if the reaction is carried out at a lower temperature to secure the quality of the product, the reaction rate will be low, and an excessive capacity of the reactor is required to attain the predetermined productivity, or an unreacted alkylene carbonate tends to remain in the product.

Whereas, if ethylene carbonate remains after the hydrolysis in the course of production of ethylene glycol which is industrially most important, it forms an azeotropic mixture together with ethylene glycol, whereby their separation or purification tends to be difficult.

Further, in the hydrolysis of an alkylene carbonate, it is common to employ a molar ratio of water to an alkylene carbonate in the charged starting materials within a range of from about 1.3:1 to about 5.0:1. If the molar ratio is less than this range, there will be a problem that as the reaction proceeds, water will be consumed, and the water concentration will decrease, whereby the reaction rate decreases, so that it takes time to complete the reaction, and the amount of impurities formed, tends to increase. On the other hand, if water is charged in a large amount beyond this range, water will be present in the system in an amount substantially exceeding the amount consumed for the reaction, whereby there will be a problem that a large quantity of heat will be required for heating the reaction solution and separating water in the purification system.

Further, the alkylene carbonate to be used as the starting material, can be obtained by reacting an alkylene oxide with carbon dioxide gas in the presence of a carbonating catalyst. However, in a case where this step and the hydrolyzing step are carried out continuously, if the carbonating catalyst is used by recycling, the carbonating catalyst activities will gradually decrease. Accordingly, it is desired to develop a process whereby the catalyst activities will not decrease.

SUMMARY OF THE INVENTION

It is an object of the present invention to provide a process for producing an alkylene glycol, which is free from the above described problems. Specifically, it is an object of the present invention to provide a process whereby the energy consumption is suppressed, the carbonating catalyst can be used repeatedly by recycling without deterioration of the activities even in a case where an alkylene carbonate obtained by reacting an alkylene oxide with carbon dioxide gas in the presence of the carbonating catalyst, is used, and the hydrolysis can be completed efficiently at a low temperature in a short period of time.

The present inventors have conducted extensive studies to solve the above problems and, as a result, have found it possible to suppress the energy consumption and to maintain the reaction rate at a high level by maintaining the water concentration in the reaction system within a certain range in a certain range of conversion of the alkylene carbonate. The present invention has been accomplished on the basis of this discovery.

That is, the object of the present invention can be accomplished by a process for producing an alkylene glycol, which is a continuous process for producing an alkylene glycol comprising the following steps (1) to (4), wherein the hydrolysis step (2) is divided into a plurality of stages, and the hydrolysis is carried out so that the water concentration in the reaction stage wherein the conversion of the alkylene carbonate is at least 60%, is from 15 to 30 wt %:

(1) a carbonating step of reacting an alkylene oxide with carbon dioxide gas in the presence of a carbonating catalyst to form a reaction solution containing an alkylene carbonate, (2) a hydrolysis step of hydrolyzing the reaction solution obtained in step (1) while releasing carbon dioxide gas, to form an aqueous alkylene glycol solution, (3) a distillation step of distilling the aqueous alkylene glycol solution to obtain at least a dehydrated alkylene glycol and a solution containing the carbonating catalyst, and (4) a recycling step of supplying the solution containing the carbonating catalyst to the carbonating step (1).

DETAILED DESCRIPTION OF THE INVENTION

Now, the present invention will be described in detail.

In the present invention, firstly, an alkylene oxide is reacted with carbon dioxide gas in the presence of a catalyst to form a reaction solution containing an alkylene carbonate. Preferably, an alkylene oxide is reacted with carbon dioxide gas and water to form a reaction solution containing an alkylene carbonate and an alkylene glycol. This reaction can be carried out in accordance with a known method.

The catalyst to be employed, may, for example, be an alkali metal bromide or iodide, an alkaline earth metal bromide or iodide, an ammonium halide such as tributylmethylammonium iodide, or a phosphonium halide such as tributylmethylphosphonium iodide. Among them, a quaternary phosphonium halide is particularly preferred, and usually one represented by the following formula is employed.

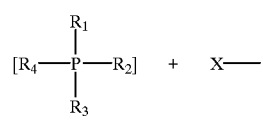

In the above formula, each of $R_1$ to $R_4$ which are independent of one another, represents a group such as an alkyl group, an alkenyl group, an aryl group or an aralkyl group, which may have a substituent inert to the reaction, bonded. X is chlorine, bromine or iodine.

Specific examples of such a quaternary phosphonium halide may be those disclosed on pages 2 and 3 of JP-A-58-22448. Among them, particularly preferred is a tetraalkylphosphonium halide wherein each of R1 to R4 which are independent of one another, is a $C_{1-6}$ alkyl group. The quaternary phosphonium halide is usually synthesized outside the system and then added to the system. If desired, however, the corresponding tertiary phosphine and alkyl halide may be added to the reaction system, so that the quaternary phosphonium halide is formed in the reaction system. As the carbonating catalyst, the quaternary phosphonium halide may usually be used alone, but if desired, other promoter or cocatalyst component may be used in combination. For example, the quaternary phosphonium halide may be used in combination with from 0.01 to 1 molar time of an alkali metal carbonate, whereby it is possible to reduce formation of a by-product such as diethylene glycol in the carbonating step, and to promote the reaction in the hydrolytic step.

The reaction of the carbonating step is carried out usually from 70 to 200° C., preferably from 100 to 170° C., more preferably from 100 to 150° C. If the reaction temperature is low, the reaction rate tends to be low. On the other hand, if the reaction temperature is too high, side reactions will increase, and a loss due to decomposition of the catalyst will increase. The reaction pressure is usually from 5 to 50 kg/cm$^2$G (0.59 to 5.0 MPa), preferably from 10 to 30 kg/cm$^2$G (from 1.08 to 3.04 MPa). As the reaction pressure becomes high, the reaction rate of an alkylene oxide usually increases, and formation of a by-product such as a dialkylene glycol usually decreases. However, to carry out the reaction under a high pressure, it will be required to employ an expensive reactor and other instruments, and the cost for the power required to compress carbon dioxide gas will increase.

The molar ratio of carbon dioxide gas to the alkylene oxide supplied to the reaction system, is usually at most 5, preferably at most 3. If this molar ratio is large, the reaction proceeds satisfactorily, but the cost for the power to compress the carbon dioxide gas will increase. Even if this molar ratio is less than 1, the reaction will proceed. However, the carbon dioxide gas not only serves as a starting material for the reaction but also serves to stir the reaction system thereby to prevent a local increase of the temperature. Accordingly, the carbon dioxide gas is preferably supplied in a molar ratio of at least 0.5, more preferably at least 1.0, to ethylene oxide. As mentioned above, it is preferred to supply water to the reaction system. The ratio of water to the alkylene oxide is optional, but usually it is in a molar ratio of at most 10, preferably at most 5. If this molar ratio is large, the concentration of the aqueous alkylene glycol solution obtainable via the subsequent hydrolyzing step, will decrease, and a substantial cost will be required for removal of water. On the other hand, even if the molar ratio is less than 1, i.e. even when water is supplied only in an amount of less than equimolar to the alkylene oxide, the reaction will proceed. However, it is advantageous that the amount of water supplied is large to some extent, also from the viewpoint of control of the reaction temperature.

As the reactor, a reactor of any optional type may be employed so long as it provides good gas-liquid contact. It is preferred to employ a bubble column reactor, so that the alkylene oxide, the carbon dioxide gas, the catalyst and the water are supplied to the bottom of the reactor, and from the top, the formed reaction solution and excess carbon dioxide gas are withdrawn. The reaction solution is sent to the subsequent hydrolyzing step, and the carbon dioxide gas will be recycled to the bubble column reactor after being supplemented to compensate the consumed amount. The reaction is a highly exothermic reaction, and it is accordingly preferred to control the reaction temperature by an external cooling system such that the reaction solution is withdrawn from the tower top, cooled by a heat exchanger and then returned to the bottom of the reactor.

Then, the reaction solution containing the alkylene carbonate, obtained as described above, is hydrolyzed while releasing carbon dioxide gas, to form an aqueous alkylene glycol solution. The hydrolysis of the alkylene carbonate is represented by the following formula (1).

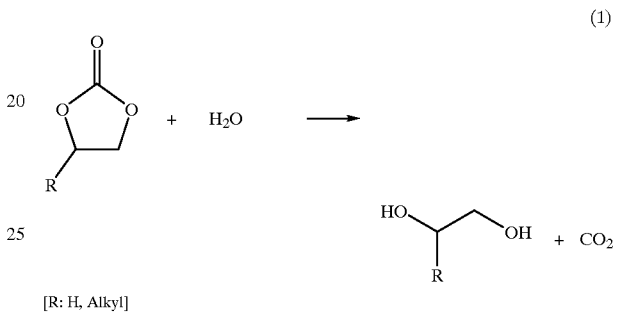

[R: H, Alkyl]

In a conventional reaction system wherein the hydrolysis is completed in one stage or, even in the case of a multi-stage reaction, the reaction is completed only with the charged water without controlling the water concentration, the water concentration decreases with the progress of the reaction, and the reaction rate gradually decreases, whereby it takes time to complete the reaction. If the water concentration in the charged starting material is increased to prevent the decrease in the reaction rate, there will be a problem that a large quantity of heat energy will be required for separating water in a purification system and for heating the reaction solution, as mentioned above.

In the present invention, the hydrolysis step is divided into a plurality of stages, and the water concentration in a reaction stage wherein the conversion of the alkylene carbonate is at least 60%, is maintained to be within a range of from 15 to 30 wt %.

If this water concentration becomes to be less than 15 wt % in the reaction stage with such a predetermined conversion, the reaction rate tends to decrease, as mentioned above. On the other hand, even if it is increased beyond 30 wt %, no further improvement in the reaction rate corresponding to the increased amount will be obtained, and the above mentioned energy load will increase, such being inefficient.

The method for maintaining the water concentration within the range specified by the present invention, may, for example, be a method wherein the progress of the hydrolysis and the consumption of water are separately monitored by experiments, and the corresponding amount of water is continuously or intermittently added, or a method wherein the amount of water in the system is timely checked, and a required amount of water is added depending upon the checked result.

The method for adding water to the system may, for example, be a method wherein water pressurized by e.g. a pump, which is preferably preliminarily heated to maintain the reaction temperature to be constant, is supplied into the reactor, or a method wherein steam having a vapor pressure of at least the reaction pressure, is blown into the reaction system. However, the method for addition is not particularly limited. For selection of the method for adding water, it is advisable to select a suitable method for every reaction stage taking the following into consideration.

In the present invention, it is preferred to carry out the reaction by dividing the hydrolysis step into a plurality of stages, and adjusting the reaction pressure for each of the second and subsequent reaction stages to be at most the reaction pressure of the preceding reaction stage, provided that the reaction pressure of at least one reaction stage among the second and subsequent reaction stages, is adjusted to be lower than the pressure of the preceding reaction stage. The reaction will be accelerated, such being desirable. This is believed to be attributable to the fact that the carbon dioxide gas can be efficiently removed out of the system by lowering the reaction pressure within a range where no boiling of the system takes place. To adjust the reaction pressure of the second or subsequent stages to be lower than the reaction pressure of the preceding stage, it is preferred to adjust the pressure to be from 20 to 90% of the pressure of the preceding stage.

If the pressure of a certain reaction stage is adjusted to be so low that it is less than 20% of the pressure of the preceding stage, boiling of the reaction solution is likely to take place. On the other hand, if it exceeds 90%, the effect of lowering the pressure tends to be small, and the reaction rate is likely to be low.

In the present invention, the reaction pressure in each of the plurality of divided reaction stages, is preferably at least the vapor pressure of the reaction solution in that stage. If the reaction pressure is lower than this vapor pressure, the reaction solution is likely to boil, and the concentration of water in the liquid phase tends to decrease, whereby the hydrolysis rate tends to decrease, and the heat for heating will be consumed as heat of vaporization, such being disadvantageous from the viewpoint of energy consumption. Here, the vapor pressure of the reaction solution is a saturated vapor pressure calculated from the temperature of the reaction stage and the composition of the reaction solution excluding carbon dioxide gas.

The hydrolysis pressure in the present invention is adjusted usually from 0.1 to 5 MPa, preferably from 0.2 to 3 MPa. If the reaction pressure is less than 0.1 MPa, boiling of the reaction solution is likely to take place, as mentioned above. On the other hand, if the reaction pressure is made higher than 5 MPa, the installation cost will increase to secure pressure resistance, etc., such being uneconomical.

In the process of the present invention, the temperature for the hydrolysis is preferably adjusted within a range of from 50 to 200° C. If the reaction temperature is lower than 50° C., the reaction rate will be low, such being not practical. On the other hand, if the reaction is carried out at a high temperature exceeding 200° C., the quality of an alkylene glycol as the product tends to be poor in many cases. For a better balance of the reaction rate and the quality of the product, the reaction temperature is preferably within a range of from 80 to 180° C., more preferably within a range of from 100 to 180° C.

This hydrolysis is an endothermic reaction, and to maintain the reaction temperature in order to proceed with the reaction, it is necessary to heat the system. As a method for such heating, it is common to employ a method of indirectly heating via e.g. a jacket or a coil by a heat source such as high pressure steam or an electric heater, or a method of directly heating by blowing steam having a vapor pressure of at least the reaction pressure into the reaction system. In a case where the water concentration is high beyond 30 wt %, it is preferred to employ an indirect heating method by an external heat source. Even if steam is blown into a system having a high water content, most of the supplied water is likely to pass through without being absorbed, whereby the efficiency will be low.

In a reaction stage where the water concentration in the system has become at most 30 wt %, it is effective to employ a direct heating method of blowing steam into the system, as the heating and supply of water can simultaneously be carried out. Among a plurality of divided reaction stages, it is at a reaction stage where the conversion of the alkylene carbonate becomes at least 60% that the water concentration in the system is maintained in the specified range. In a reaction stage where the conversion of the alkylene carbonate is lower than 60%, the alkylene carbonate concentration in the system is high, and the reaction rate is governed by this alkylene carbonate concentration, and the influence of the water concentration will be subsidiary, whereby the necessity to maintain the water concentration within the specified range is low, and the effect is also small.

As a reactor which can be employed for the process of the present invention, a vessel type reactor, a multi stage tower type reactor or a reaction distillation tower may, for example, be mentioned. In a reactor of any type, it is necessary to efficiently separate carbon dioxide gas generated by the hydrolysis, from the reaction system.

In the process of the present invention, the number of the hydrolysis stages is preferably from 2 to 8 stages. If the number of stages exceeds 8 stages, the installation costs will be substantial, and there will be a problem that control of the reaction process tends to be complicated. As a method for dividing the reaction step into a plurality of stages, it is common to provide a plurality of reactors corresponding to the number of stages. However, it is also possible to employ a single reactor divided into a plurality of sections by means of e.g. partition walls.

The aqueous alkylene glycol solution discharged from the hydrolytic reactor is subjected to distillation by a usual method to obtain a dehydrated alkylene glycol and a solution containing the catalyst, and the solution containing the catalyst is supplied, as a catalyst solution, to the step of forming an alkylene carbonate from the alkylene oxide and carbon dioxide gas.

From the hydrolytic reactor, carbon dioxide gas formed by the hydrolysis will be discharged, but it will be accompanied by water and an alkylene glycol. In the present invention, this gas is cooled to form a condensed liquid or washed to obtain a solution containing the alkylene glycol. The cooling for condensation or washing is carried out so that the alkylene glycol in the gas will be at most 20 ppm. For the purpose of recovery of the alkylene glycol, it is economical to carry out this cooling for condensation or the washing under mild conditions. However, in such a case, even if the obtained condensed liquid or the washing liquid is returned to the system, the effects for suppressing the deterioration of the catalyst activities tend to be small.

The solution containing the alkylene glycol, obtained by the cooling or washing of the gas, is supplied to an optional position from the step of forming an alkylene carbonate from an alkylene oxide and carbon dioxide gas to the step of distilling the aqueous alkylene glycol solution to obtain a solution containing the catalyst. Preferably, it is supplied to the hydrolytic reactor or to the distillation system wherein the solution containing the catalyst is obtained from the aqueous ethylene glycol solution. In such a way, it is possible to suppress the deterioration of the activities of the carbonating catalyst to be used by recycling. Namely, in the gas discharged from the hydrolytic reactor, a component for suppressing the deterioration of the catalyst activities, is contained, and this component is dissolved and recovered in the solution obtained by cooling or washing the gas and finally recycled to the zone where ethylene carbonate is formed from ethylene oxide and carbon dioxide gas, whereby the deterioration of the catalyst activities is believed to be suppressed. It is not known what is this component. However, in the gas discharged from the hydrolytic zone, a halogen which is believed to be attributable to the catalyst, is contained, and this halogen will transfer to the liquid under the above mentioned cooling or washing conditions, and accordingly, it is believed that at least a part of suppressing the deterioration of the catalyst activities, is attributable to the action of this halogen.

As another method for producing an alkylene glycol, a method is known wherein an alkylene oxide and water are reacted in the presence of carbon dioxide. However, this reaction involves an alkylene carbonate as an intermediate, and it is regarded as one of the embodiments of the present invention to adjust the water content within a range of from 15 to 30 wt % in the stage of completing the reaction to obtain an alkylene glycol by this reaction method. Further, there will be an effect of the present invention such that the hydrolysis of the remaining alkylene carbonate can efficiently be carried out.

The conversion of the alkylene carbonate in such a case, is a conversion with respect to the amount of the alkylene carbonate as calculated as the entire amount of the alkylene oxide has converted to the alkylene carbonate.

As the alkylene carbonate as the starting material in the process of the present invention, one having an alkylene group with from 2 to 30 carbon atoms, is preferred. Among them, industrially important ethylene carbonate or propylene carbonate is preferred. The effects of the present invention are particularly good when applied to ethylene carbonate having a characteristic of being azeotropically distilled with water.

Further, it may have one or more alkyl groups having from 1 to 12 carbon atoms, as substituents on the alkylene group.

According to the process of the present invention, the final conversion of the alkylene carbonate can be made to be about 100%, and especially, the conversion of the alkylene carbonate at a later stage can be made to be about 100%.

Namely, according to the process of the present invention, the hydrolysis of the alkylene carbonate can be facilitated, whereby it is possible to produce an alkylene glycol efficiently in a reactor of a small capacity or in a shorter period of residence time. Further, the activities of the carbonating catalyst can be maintained even when the catalyst is used repeatedly by recycling.

BRIEF DESCRIPTION OF THE DRAWINGS

In FIG. 1, reference numeral 1 indicates a bubble column type carbonating reactor, numeral 2 a carbon dioxide gas supply pipe, numeral 3 a supply pipe for e.g. alkylene oxide, numeral 4 a heat exchanger, numeral 5 a pipe for recycling the reaction solution, numeral 6 a discharge pipe, numeral 7 a gas-liquid separator, numeral 8 a hydrolyzing apparatus, numeral 9 a distillation tower, numeral 10 a flushing vessel, numeral 11 a pipe for supplying the gas to a cooler, numeral 12 the cooler, and numeral 13 a pipe for supplying a condensed liquid.

EXAMPLES

Figure 1:
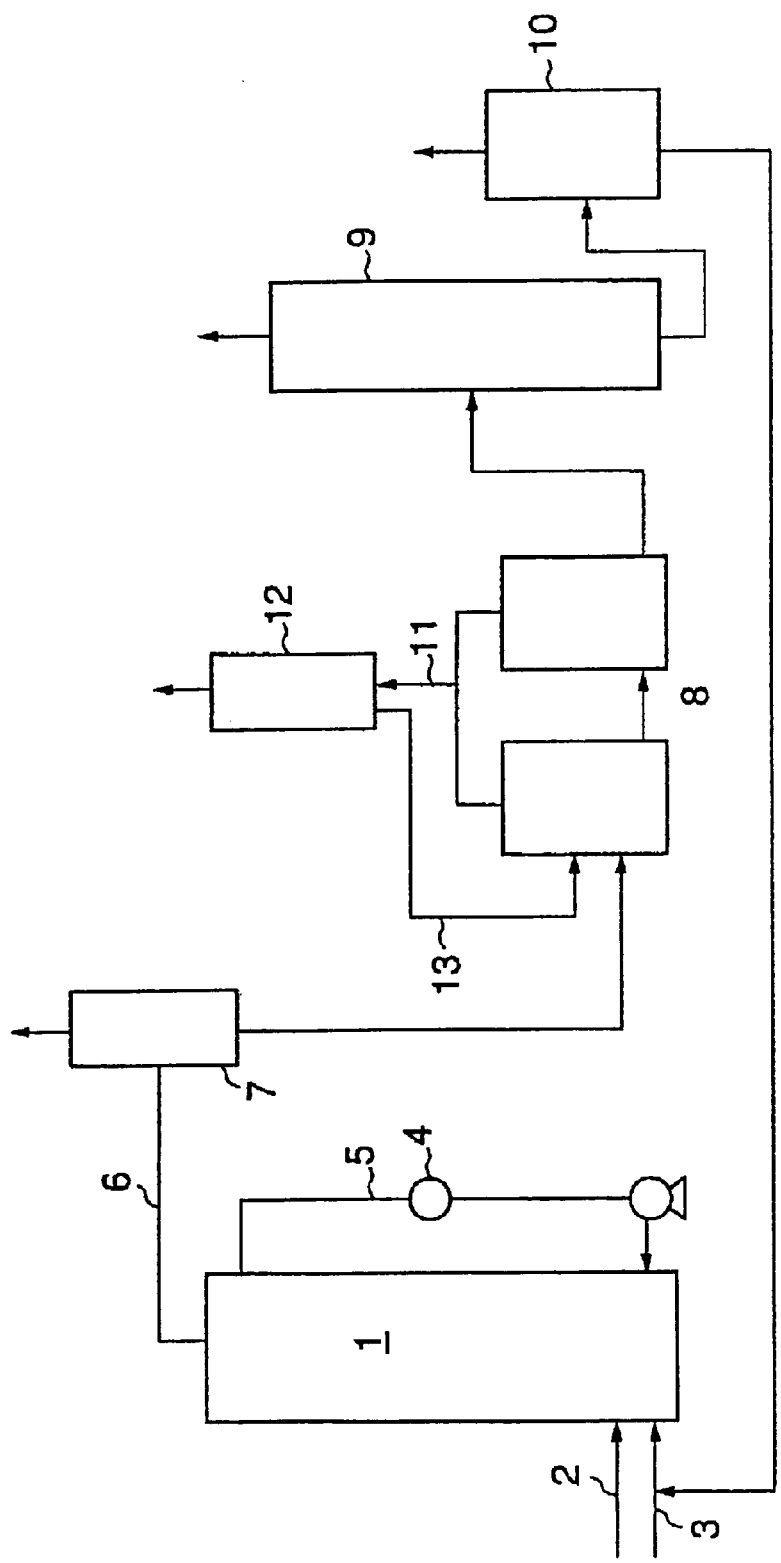
FIG. 1 is an example of a flow sheet for carrying out the present invention.

Now, the present invention will be described in further detail with reference to Examples. However, it should be understood that the present invention is by no means restricted to such specific Examples.

Example 1

Ethylene glycol was prepared from ethylene oxide, carbon dioxide gas and water in accordance with the flow sheet shown in FIG. 1.

To a bubble column type reactor 1 (inner diameter: 20 cm, effective height: 200 cm), carbon dioxide gas was continuously supplied from a pipe 2, and ethylene oxide, water and a circulating catalyst solution were continuously supplied from a pipe 3. The respective amounts supplied, were 140 kg/hr of carbon dioxide gas, 62 kg/hr of ethylene oxide, 50 kg/hr of water and about 9.0 kg/hr of the circulating catalyst solution (as tributylmethylphosphonium iodide: about 4.5 kg/hr, and as potassium carbonate: 0.18 kg/hr). The reaction was carried out at 110° C. under 2.06 MPa, and the reaction temperature was controlled by circulating a part of the reaction solution through an external circulation pipe including a heat exchanger 4.

Via a pipe 6, the reaction solution was sent to a gas-liquid separator 7 for gas-liquid separation and then supplied to a hydrolyzing apparatus 8. The hydrolyzing apparatus comprised two vessel type reactors connected in series, and the conditions for hydrolysis in the respective stages were controlled so that the first stage was carried out at 150° C. under 0.55 MPa, and the second stage was carried out at 150° C. under 0.25 MPa. Further, the reaction was carried out by blowing steam into each reactor so that the water concentration in each reactor was within a range of from 15 to 30 wt %.

As a result, the conversion of ethylene carbonate was 93.0% at the outlet of the first stage hydrolytic reactor and about 100% (detection limit by gas chromatography: less than 10 ppm) at the outlet of the second stage reactor. The water concentrations at that time were 18.8% and 19.2% respectively.

The aqueous ethylene glycol solution obtained from the hydrolyzing apparatus, was subjected to distillation firstly in a distillation tower 9 under a tower top pressure of 80 mmHg and at the tower bottom temperature of 140° C. to distill water, and the tower bottom eluted solution was supplied to a flushing vessel maintained under 62 mmHg to evaporate most of ethylene glycol and diethylene glycol, and a solution containing tributylmethylphosphonium iodide as the catalyst remaining without being evaporated, was recovered and recycled to the reactor 1.

Further, the gas discharged from the hydrolyzing apparatus was supplied to a cooler 12 via a pipe 11 and cooled to condensate water and ethylene glycol contained therein, and an aqueous solution containing 6.2% of ethylene glycol was recovered at a rate of 27 kg/hr and supplied to the first stage of the hydrolyzing apparatus via a pipe 13. The temperature of the gas discharged from the cooler was 39° C., and the ethylene glycol concentration was 4 ppm.

In this way, the reaction was carried out for 90 days, whereby the conversion of ethylene oxide in the reactor 1 was initially 99.5% and 99.4% even after 90 days.

Comparative Example 1

The reaction was carried out in the same manner as described above except that in Example 1, the operation of returning the condensed liquid formed by cooling the gas discharged from the hydrolyzing apparatus, to the hydrolyzing apparatus, was omitted. The conversion of ethylene oxide which was initially 99.5%, decreased to 98.1% after 90 days.

Comparative Example 2

An experiment for the production of ethylene glycol was carried out in the same manner as Example 1 except that control of the water concentration in the later stage hydrolysis reactor was omitted, and accordingly without supplying water, heating of the later stage reactor to maintain the reaction temperature of the later stage, was carried out solely by an electric heater.

The water concentration in the later stage reactor was 13.7%, and the overall conversion of ethylene carbonate at the outlet of the later stage was at a level of 99.9%, and 1,400 ppm of ethylene carbonate was included in ethylene glycol purified from the formed solution thus obtained.

What is claimed is:

1. A process for producing an alkylene glycol, which is a continuous process for producing an alkylene glycol comprising the following steps (1) to (4), wherein the hydrolysis step (2) is divided into a plurality of stages, and the hydrolysis is carried out so that the water concentration in a reaction stage wherein the conversion of the alkylene carbonate is at least 60%, is from 15 to 30 wt %:

(1) a carbonating step of reacting an alkylene oxide with carbon dioxide gas in the presence of a carbonating catalyst to form a reaction solution containing an alkylene carbonate, (2) a hydrolysis step of hydrolyzing the reaction solution obtained in step (1) while releasing carbon dioxide gas, to form an aqueous alkylene glycol solution, (3) a distillation step of distilling the aqueous alkylene glycol solution to obtain at least a dehydrated alkylene glycol and a solution containing the carbonating catalyst, and (4) a recycling step of supplying the solution containing the carbonating catalyst to the carbonating step (1).

2. The process for producing an alkylene glycol according to claim 1, wherein in the hydrolysis step divided into a plurality of stages, the reaction pressure in each of the second and subsequent reaction stages, is adjusted to be at most the reaction pressure of the preceding reaction stage, and the reaction pressure of at least one reaction stage among them is adjusted to be lower than the pressure of the preceding reaction stage.

3. The process for producing an alkylene glycol according to claim 1, wherein in the hydrolysis step divided into a plurality of stages, the pressure of at least one reaction step among the second and subsequent reaction stages, is adjusted to be from 20 to 90% of the pressure of the preceding reaction stage.

4. The process for producing an alkylene glycol according to claim 1, wherein the reaction pressure in each of the plurality of divided hydrolysis stages is within a range of from 0.1 MPa to 5 MPa.

5. The process for producing an alkylene glycol according to claim 1, wherein the reaction temperature in each of the plurality of divided hydrolysis stages is within a range of from 50 to 200° C.

6. The process for producing an alkylene glycol according to claim 1, wherein the alkylene carbonate is ethylene carbonate or propylene carbonate.

7. The process for producing an alkylene glycol according to claim 1, wherein a quaternary phosphonium halide is used as the carbonating catalyst.

8. The process for producing an alkylene glycol according to claim 7, wherein the gas containing carbon dioxide gas released in each of the plurality of divided hydrolysis stages, is cooled and condensed or is washed with a washing liquid, so that the alkylene glycol in the gas becomes to be at most 20 ppm, to obtain a solution containing the alkylene glycol, which is supplied to any one of steps (1) to (4).

9. The process for producing an alkylene glycol according to claim 7, wherein water is supplied to the carbonating step to let an alkylene carbonate and an alkylene glycol form.

10. The process for producing an alkylene glycol according to claim 8, wherein the solution containing the alkylene glycol, obtained by cooling and condensing the gas or by washing the gas with a washing liquid, is supplied to step (2) or (3).

* * * * *